US010780417B2

(12) United States Patent
Kim et al.

(10) Patent No.: US 10,780,417 B2
(45) Date of Patent: *Sep. 22, 2020

(54) SUPER ABSORBENT POLYMER

(71) Applicant: LG Chem, Ltd., Seoul (KR)

(72) Inventors: Ju Eun Kim, Daejeon (KR); Gi Cheul Kim, Daejeon (KR); Won Mun Choi, Daejeon (KR); Ki Hyun Kim, Daejeon (KR); Seul Ah Lee, Daejeon (KR); Won Taeck Lim, Daejeon (KR)

(73) Assignee: LG Chem, Ltd. (KR)

( * ) Notice: Subject to any disclaimer, the term of this patent is extended or adjusted under 35 U.S.C. 154(b) by 0 days.

This patent is subject to a terminal disclaimer.

(21) Appl. No.: 16/084,098

(22) PCT Filed: Jan. 5, 2017

(86) PCT No.: PCT/KR2017/000155
§ 371 (c)(1),
(2) Date: Sep. 11, 2018

(87) PCT Pub. No.: WO2018/074669
PCT Pub. Date: Apr. 26, 2018

(65) Prior Publication Data
US 2019/0091656 A1 Mar. 28, 2019

(30) Foreign Application Priority Data

Oct. 19, 2016 (KR) .......................... 10-2016-0135841
Dec. 26, 2016 (KR) .......................... 10-2016-0179500

(51) Int. Cl.
| | |
|---|---|
| *B01J 20/26* | (2006.01) |
| *C08L 33/08* | (2006.01) |
| *C08F 2/44* | (2006.01) |
| *C08J 3/24* | (2006.01) |
| *C08J 3/075* | (2006.01) |
| *C08J 3/12* | (2006.01) |
| *C08K 3/34* | (2006.01) |
| *C08K 3/00* | (2018.01) |
| *C08K 5/11* | (2006.01) |
| *B01J 20/10* | (2006.01) |
| *B01J 20/28* | (2006.01) |
| *B01J 20/30* | (2006.01) |
| *A61L 15/18* | (2006.01) |
| *A61L 15/60* | (2006.01) |
| *A61L 15/24* | (2006.01) |
| *C08F 220/06* | (2006.01) |
| *B01J 13/16* | (2006.01) |

(52) U.S. Cl.
CPC ............ *B01J 20/267* (2013.01); *A61L 15/18* (2013.01); *A61L 15/24* (2013.01); *A61L 15/60* (2013.01); *B01J 13/16* (2013.01); *B01J 20/103* (2013.01); *B01J 20/28021* (2013.01); *B01J 20/3021* (2013.01); *B01J 20/3085* (2013.01); *C08F 2/44* (2013.01); *C08F 220/06* (2013.01); *C08J 3/075* (2013.01); *C08J 3/12* (2013.01); *C08J 3/24* (2013.01); *C08K 3/00* (2013.01); *C08K 3/34* (2013.01); *C08K 5/11* (2013.01); *C08L 33/08* (2013.01); *C08J 2333/08* (2013.01)

(58) Field of Classification Search
CPC ................. B01J 20/267; B01J 20/3085; B01J 20/28021; B01J 20/103; B01J 13/16; B01J 20/3021; C08K 5/11; C08K 3/00; C08K 3/34; C08F 2/44; C08F 220/06; C08L 33/08; A61L 15/18; A61L 15/24; A61L 15/60; C08J 2333/08; C08J 3/12; C08J 3/075; C08J 3/24
See application file for complete search history.

(56) References Cited

U.S. PATENT DOCUMENTS

| | | | |
|---|---|---|---|
| 7,638,570 B2 | 12/2009 | Torii et al. |
| 7,812,082 B2 | 10/2010 | McIntosh et al. |
| 7,906,585 B2 | 3/2011 | McIntosh et al. |
| 8,222,477 B2 | 7/2012 | Azad et al. |
| 8,962,910 B2 | 2/2015 | Azad et al. |
| 9,309,375 B2 | 4/2016 | Ikeuchi et al. |
| 9,517,446 B2 | 12/2016 | Won et al. |
| 9,580,519 B2 | 2/2017 | Nogi et al. |
| 2006/0204755 A1 | 9/2006 | Torii et al. |
| 2007/0135554 A1 | 6/2007 | McIntosh et al. |

(Continued)

FOREIGN PATENT DOCUMENTS

| | | |
|---|---|---|
| CN | 101094695 A | 12/2007 |
| CN | 101326234 A | 12/2008 |

(Continued)

OTHER PUBLICATIONS

Third Party Observation of PCT/KR2017/000157 dated Feb. 20, 2019.
Extended European Search Report including WQritten Opinion for EP17862793.1 dated Feb. 20, 2019.
Extended European Search Report including Written Opinion for EP16919147.5 dated Feb. 28, 2019.
Extended European Search Report including Written Opinion for EP17863185.9 dated Feb. 28, 2019.
Extended European Search Report including Written Opinion for EP17861873.2 dated Feb. 28, 2019.

(Continued)

*Primary Examiner* — Andrew J. Oyer
(74) *Attorney, Agent, or Firm* — Lerner, David, Littenberg, Krumholz & Mentlik, LLP

(57) ABSTRACT

The present invention relates to superabsorbent polymer having excellent centrifuge retention capacity and permeability. The superabsorbent polymer simultaneously exhibits excellent centrifuge retention capacity and permeability, and thus, can fundamentally solve the problems of the existing superabsorbent polymer and technical requirement of the art, and can provide various hygienic goods exhibiting more excellent properties.

4 Claims, No Drawings

(56) References Cited

U.S. PATENT DOCUMENTS

| | | |
|---|---|---|
| 2008/0021130 A1 | 1/2008 | McIntosh et al. |
| 2008/0045916 A1 | 2/2008 | Herfert et al. |
| 2008/0140037 A1* | 6/2008 | Newman ............. C08K 5/103 604/367 |
| 2009/0281232 A1 | 11/2009 | Ikeuchi et al. |
| 2010/0100066 A1 | 4/2010 | Azad et al. |
| 2011/0001087 A1 | 1/2011 | Hillebrecht et al. |
| 2012/0035294 A1 | 2/2012 | Kim et al. |
| 2012/0085971 A1 | 4/2012 | Daniel et al. |
| 2012/0271260 A1 | 10/2012 | Azad et al. |
| 2014/0114035 A1 | 4/2014 | Nogi et al. |
| 2014/0306156 A1 | 10/2014 | Tian et al. |
| 2015/0087742 A1 | 3/2015 | Won et al. |
| 2015/0157759 A1 | 6/2015 | Azad et al. |
| 2015/0210824 A1* | 7/2015 | Wang ................... C08K 3/346 428/402 |
| 2015/0218341 A1 | 8/2015 | Nakashima et al. |
| 2015/0225514 A1 | 8/2015 | Kimura et al. |
| 2016/0096944 A1 | 4/2016 | Wattebled et al. |
| 2016/0361704 A1 | 12/2016 | Won et al. |
| 2017/0073478 A1 | 3/2017 | Joo et al. |
| 2017/0326528 A1 | 11/2017 | Park et al. |
| 2017/0361305 A1 | 12/2017 | Kim et al. |

FOREIGN PATENT DOCUMENTS

| | | |
|---|---|---|
| CN | 100503663 C | 6/2009 |
| CN | 102471394 A | 5/2012 |
| CN | 105283490 A | 1/2016 |
| DE | 10013217 A1 | 9/2001 |
| EP | 0398653 B1 | 3/1996 |
| EP | 3056268 A1 | 8/2016 |
| JP | H0725935 A | 1/1995 |
| JP | 2888866 B2 | 5/1999 |
| JP | 3439234 B2 | 8/2003 |
| JP | 2003235889 A | 8/2003 |
| JP | 2004091613 A | 3/2004 |
| JP | 2008522003 A | 6/2008 |
| JP | 2009051952 A | 3/2009 |
| JP | 2009057496 A | 3/2009 |
| JP | 2009114391 A | 5/2009 |
| JP | 2013540186 A | 10/2013 |
| JP | 5367364 B2 | 12/2013 |
| JP | 5502762 B2 | 5/2014 |
| JP | 2016056251 A | 4/2016 |
| JP | 2016056313 A | 4/2016 |
| KR | 100148487 B | 12/1998 |
| KR | 20050107415 A | 11/2005 |
| KR | 20080092341 A | 10/2008 |
| KR | 20110006771 A | 1/2011 |
| KR | 20110086057 A | 7/2011 |
| KR | 20130018350 A | 2/2013 |
| KR | 20130120400 A | 11/2013 |
| KR | 101358296 B1 | 2/2014 |
| KR | 20150050565 A | 5/2015 |
| KR | 20150056572 A | 5/2015 |
| KR | 20150116418 A | 10/2015 |
| KR | 20160004967 A | 1/2016 |
| KR | 20160010516 A | 1/2016 |
| KR | 20160016645 A | 2/2016 |
| KR | 20160016714 A | 2/2016 |
| KR | 20160068768 A | 6/2016 |
| KR | 20160091242 A | 8/2016 |
| WO | 2006062609 A2 | 6/2006 |
| WO | 2006094907 A1 | 9/2006 |
| WO | 2012082879 A1 | 6/2012 |
| WO | 2012082884 A1 | 6/2012 |
| WO | 2012144595 A1 | 10/2012 |

OTHER PUBLICATIONS

George Odian, "Principles of Polymerization", A Wiley-Interscience Publication, Second Edition, 1981, p. 203.

Ki Hyun Kim et al., U.S. Appl. No. 16/083,755, filed Sep. 10, 2018, titled "Preparation Method of Super Absorbent Polymer".

Kyu Pal Kim et al., U.S. Appl. No. 16/083,749, filed Sep. 10, 2018, titled "Super Absorbent Polymer".

Kyu Pal Kim et al., U.S. Appl. No. 16/084,111, filed Sep. 11, 2018, titled "Super Absorbent Polymer".

Reinhold Schwalm, "UV Coatings: Basics, Recent Developments and New Applications", Dec. 21, 2006, p. 115.

Search report from International Application No. PCT/KR2016/015234, dated Jul. 17, 2017.

Search report from International Application No. PCT/KR2017/000155, dated Jul. 17, 2017.

Search report from International Application No. PCT/KR2017/000156, dated Jul. 19, 2017.

Search report from International Application No. PCT/KR2017/000157, dated Jul. 19, 2017.

Search Report from Chinese Office Action for Application No. 201780017677.8 dated Jul. 10, 2020; 3 pages.

* cited by examiner

SUPER ABSORBENT POLYMER

CROSS-REFERENCE TO RELATED APPLICATION

This application is a national phase entry under 35 U.S.C. § 371 of International Application No. PCT/KR2017/000155, filed Jan. 5, 2017, which claims priority to Korean Patent Application No. 10-2016-0135841, filed Oct. 19, 2016, and Korean Patent Application No. 10-2016-0179500, filed on Dec. 26, 2016, the disclosures of which are incorporated herein by reference.

BACKGROUND OF THE INVENTION (a) Field of the Invention

The present invention relates to superabsorbent polymer exhibiting excellent centrifuge retention capacity and permeability.

(b) Description of the Related Art

Super absorbent polymer (SAP) is synthetic polymer material that can absorb moisture of 500 to 1000 times of self-weight, and is also named differently as super absorbency material (SAM), absorbent gel material (AGM), etc. according to developing companies. The superabsorbent polymer began to be commercialized as sanitary items, and currently, it is being widely used as hygienic goods such as a disposable diaper and so on, water-holding material for soil, water stop material for civil engineering and architecture, sheets for raising seedling, freshness preservatives in the field of food circulation, fomentation material, etc.

In most cases, such superabsorbent polymer is being widely used in the field of hygienic goods such as a diaper or sanitary pad, etc., and for such use, it is required to exhibit high absorption powder to moisture, etc., and the absorbed moisture should not escape even under external pressure, and besides, it should properly maintain the shape even when it absorbs water and the volume is expanded (swollen), thus exhibiting excellent permeability. Particularly, with the recent reduction of the amount of pulp for volume decrease of a diaper, the permeability of superabsorbent polymer is emerging as an important property.

The permeability of superabsorbent polymer can be improved by controlling the crosslinking density of superabsorbent polymer high, thus maintaining its shape even in a swollen state. However, if the crosslinking density of superabsorbent polymer is controlled high, it may be difficult to absorb moisture between the dense structures, and thus, centrifuge retention capacity may be deteriorated. For the above explained reason, there is a limit to the provision of superabsorbent polymer with simultaneously improved centrifuge retention capacity and permeability. In order to overcome this, there have been various attempts to improve these properties together by controlling the kind or use amount of an internal crosslinking agent or a surface crosslinking agent, but such attempts have reached the limit.

SUMMARY OF THE INVENTION

The present invention provides superabsorbent polymer exhibiting excellent centrifuge retention capacity and permeability.

Hereinafter, superabsorbent polymer and the preparation method thereof according to specific embodiments of the invention will be explained.

According to one embodiment of the invention, superabsorbent polymer comprising: a base resin powder comprising crosslinked polymer formed by the crosslinking polymerization of water soluble ethylenically unsaturated monomers having acid groups of which at least a part are neutralized, in the presence of an internal crosslinking agent comprising a compound represented by the following Chemical Formula 1, and inorganic material; and a surface crosslink layer on the base resin powder, formed by the additional crosslinking of the crosslinked polymer, wherein the permeability calculated by the following Calculation Formula 1 is equal to or greater than 16 mL/1 minute, is provided:

[Chemical Formula 1]

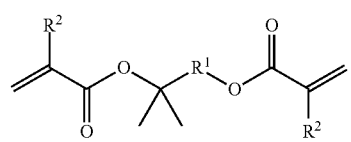

in the Chemical Formula 1, $R^1$ is a divalent organic group derived from C1-10 alkane, and $R^2$ is hydrogen or a methyl group, $$\text{Perm} = [20 \text{ mL}/T_1 \text{ (sec)}] * 60 \text{ sec} \quad \text{[Calculation Formula 1]}$$

in the Calculation Formula 1,

Perm is the permeability of superabsorbent polymer, and $T_1$ is a time (seconds) taken for a saline solution of 20 mL to pass through swollen superabsorbent polymer under pressure of 0.3 psi, after putting 0.2 g of superabsorbent polymer in a cylinder, and pouring a saline solution (0.9 wt % sodium chloride aqueous solution) so that the superabsorbent polymer is completely submerged, thus swelling the superabsorbent polymer for 30 minutes.

In general, in order to improve permeability of superabsorbent polymer, a method of controlling the crosslinking density high is used, but such a method may deteriorate centrifuge retention capacity, which is the basic property of superabsorbent polymer. Thus, as the result of experiments, the present inventors confirmed that superabsorbent polymer prepared in the presence of a heat-degradable internal crosslinking agent and inorganic material may simultaneously exhibit excellent centrifuge retention capacity and permeability, and completed the present invention.

The superabsorbent polymer according to one embodiment may have permeability calculated by the following Calculation Formula 1, of 16 mL/1 minute or more. According to the Calculation Formula 1, the permeability is defined as the amount of a saline solution passing through swollen superabsorbent polymer under pressure of 0.3 psi for 1 minute. For more specific measuring method of permeability, experimental examples described below may be referred to.

Since the superabsorbent polymer according to one embodiment exhibits excellent permeability, it is expected to exhibit excellent absorbency under load, too. Commonly, if the crosslinking density of superabsorbent polymer is controlled low, the crosslink structure may be loosened, and thus, centrifuge retention capacity may increase, but gel strength may decrease, and thus, absorbency under load may be deteriorated, and if the crosslinking density of superabsorbent polymer is controlled high, absorbency under load and permeability may increased due to dense crosslink structure, but centrifuge retention capacity may decrease. However, the superabsorbent polymer according to one embodiment, unlike the existing knowledge that centrifuge retention capacity and absorbency under load are inversely proportional to each other, may exhibit excellent properties with simultaneously improved centrifuge retention capacity and absorbency under load, etc.

For example, the superabsorbent polymer according to one embodiment may have centrifuge retention capacity (CRC) to a saline solution of 30 to 50 g/g, and absorbency under load (AUL) of 0.7 psi to a saline solution, of 15 to 30 g/g. More specifically, the superabsorbent polymer according to one embodiment may have centrifuge retention capacity (CRC) to a saline solution of 31 to 40 g/g, 32 to 40 g/g, 32.5 to 40 g/g or 33 to 40 g/g, and absorbency under load (AUL) of 0.7 psi to a saline solution, of 18 to 30 g/g, 20 to 30 g/g, 22 to 30 g/g, 23 to 30 g/g, 24 to 30 g/g or 25 to 30 g/g.

The centrifuge retention capacity (CRC) to a saline solution may be measured according to EDANA method NWSP 241.0.R2, and the absorbency under load (AUL) of 0.7 psi to a saline solution may be measured according to EDANA method NWSP 242.0.R2. For more specific measuring methods of CRC and AUL, experimental examples described below may be referred to.

The superabsorbent polymer according to one embodiment may comprise base resin powder comprising crosslinked polymer formed by the crosslinking polymerization of water soluble ethylenically unsaturated monomers having acid groups of which at least a part are neutralized, in the presence of an internal crosslinking agent comprising a compound represented by the following Chemical Formula 1, and inorganic material; and a surface crosslink layer on the base resin powder, formed by the additional crosslinking of the crosslinked polymer.

[Chemical Formula 1]

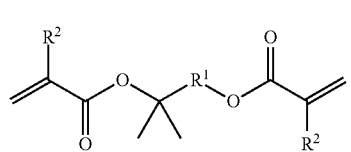

in the Chemical Formula 1, $R^1$ is a divalent organic group derived from C1-10 alkane, and $R^2$ is hydrogen or a methyl group, The compound represented by the Chemical Formula 1 is a heat-degradable internal crosslinking agent, and it may be degraded by heat. Thus, if water soluble ethylenically unsaturated monomers are subjected to crosslinking polymerization in the presence of the compound of the Chemical Formula 1, and then, introduced into subsequent process, at least a part of the crosslink structure derived from the compound of the Chemical Formula 1 in the crosslinked polymer may be degraded. Thus, the internal crosslinking density in the crosslinked polymer may decrease. To the contrary, the surface of the crosslinked polymer is additionally crosslinked by a surface crosslinking agent, and thus, the external crosslinking density increases. Thus, if crosslinking polymerization is progressed using the compound of the Chemical Formula 1 and subsequent process is conducted, the internal crosslink structure in the crosslinked polymer may be degraded, and the surface of the crosslinked polymer may be additionally crosslinked, and thus, superabsorbent polymer with crosslinking density increasing from the inside toward the outside may be obtained.

Thus prepared superabsorbent polymer may have more decreased internal crosslinking density than the base resin of the existing superabsorbent polymer. Thus, the superabsorbent polymer may exhibit relatively improved centrifuge retention capacity, compared to the existing superabsorbent polymer. And, the superabsorbent polymer may have a thicker surface crosslink layer than the existing superabsorbent polymer, because surface crosslinking is progressed before or during the degradation of internal crosslink. Thus, the superabsorbent polymer can preserve its shape well even in a swollen state, and exhibit excellent absorbency under load and permeability. Therefore, since the crosslinking density of the superabsorbent polymer of one embodiment increases from the inside toward the outside, unlike the existing knowledge that centrifuge retention capacity and permeability are inversely proportional to each other, centrifuge retention capacity and permeability are simultaneously improved, thus exhibiting both excellent properties. Consequently, the superabsorbent polymer of one embodiment can fundamentally solve the problems of the existing superabsorbent polymer and technical requirement of the art, and exhibit more excellent properties.

Hereinafter, a method for preparing superabsorbent polymer according to one embodiment of the invention will be explained in detail.

The superabsorbent polymer according to one embodiment may be prepared by the steps of: conducting crosslinking polymerization of water soluble ethylenically unsaturated monomers having acid groups of which at least a part are neutralized, in the presence of an internal crosslinking agent comprising a compound represented by the following Chemical Formula, and inorganic material, to form hydrogel polymer; drying the hydrogel polymer to form base resin powder; and additionally crosslinking the surface of the base resin powder in the presence of a surface crosslinking agent to form a surface crosslink layer:

[Chemical Formula 1]

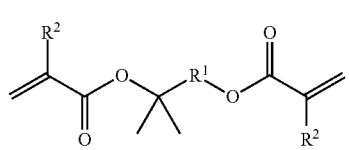

in the Chemical Formula 1, $R^1$ is a divalent organic group derived from C1-10 alkane, and $R^2$ is hydrogen or a methyl group, In the step of forming hydrogel polymer, a monomer mixture comprising water soluble ethylenically unsaturated monomers having acid groups of which at least a part are neutralized, an internal crosslinking agent, and inorganic material is subjected to crosslinking polymerization to form hydrogel polymer.

The water-soluble ethylenically unsaturated monomers may include one or more selected from the group consisting of anionic monomers and salts thereof such as (meth)acrylic acid, maleic acid, maleic anhydride, fumaric acid, crotonic acid, itaconic acid, sorbic acid, vinyl phosphinic acid, vinyl sulfonic acid, allyl sulfonic acid, 2-(meth)acryloylethane sulfonic acid, 2-(meth)acryloyloxy ethane sulfonic acid, 2-(meth)acryloyl propane sulfonic acid, or 2-(meth)acrylamido-2-methyl propane sulfonice acid; non-ionic hydrophilic group containing monomers such as (meth)acrylamide, N-substituted (meth)acrylate, 2-hydroxyethyl (meth)acrylate, 2-hydroxypropyl (meth)acrylate, methoxy polyethylene glycol (meth)acrylate, or polyethylene glycol (meth)acrylate; and amino group containing unsaturated monomers such as (N,N)-dimethylaminoethyl (meth)acrylate, (N,N)-dimethylaminopropyl (meth)acrylamide, and quarternarized products thereof.

Throughout the specification, the term 'water soluble ethylenically unsaturated monomers having acid groups of which at least a part are neutralized' means that the water soluble ethylenically unsaturated monomers include monomers having acidic groups, and at least a part of the acidic groups of the monomers having acidic groups are neutralized.

Particularly, at least a part of the water soluble ethylenically unsaturated monomers may consist of monomers (the salts of anionic monomers) in which the acidic groups included in the anionic monomers are neutralized.

More specifically, as the water soluble ethylenically unsaturated monomers, acrylic acid or salts thereof may be used, and in case acrylic acid is used, at least a part thereof may be neutralized. Due to the use of such monomers, superabsorbent polymer having more excellent properties can be prepared. For example, in case an alkali metal salt of acrylic acid is used as the water soluble ethylenically unsaturated monomers, acrylic acid may be neutralized with a neutralization agent such as caustic soda (NaOH) before use. Here, the neutralization degree of the acrylic acid may be controlled to about 50 to 95 mol %, or about 60 to 85 mol %, and within such a range, superabsorbent polymer with excellent centrifuge retention capacity can be provided without concern of precipitation during neutralization.

In the monomer mixture comprising the water-soluble ethylenically unsaturated monomers, the concentration of the water-soluble ethylenically unsaturated monomers may be controlled to about 20 to about 60 wt %, or about 25 to about 50 wt %, based on the monomer mixture comprising raw materials described below, a polymerization initiator and a solvent, etc., and may be appropriately controlled considering polymerization time and reaction conditions, etc. However, if the concentration of the monomers becomes too low, yield of superabsorbent polymer may decrease, thus causing economical problems, and if the concentration becomes too high, process problems may be generated such as precipitation of a part of the monomers or low grinding efficiency of polymerized hydrogel polymer, etc., and the properties of superabsorbent polymer may be deteriorated.

As the internal crosslinking agent, a compound represented by the Chemical Formula 1 is used so as to introduce an internal crosslink structure that can be degraded by heat into the crosslinked polymer of water soluble ethylenically unsaturated monomers.

In the Chemical Formula 1, $R^1$ is a divalent organic group derived from C1-10 alkane, and $R^2$ is hydrogen or a methyl group, as defined above, Here, the alkane may be linear, branched or cyclic alkane, and the divalent organic group derived from such alkane may be a divalent organic group wherein two hydrogen atoms are removed from one carbon, or a divalent organic group wherein each one hydrogen is removed from different carbon atoms. Specifically, $R^1$ may be methane-1,1-diyl, ethane-1,2-diyl, ethane-1,1-diyl, propane-1,3-diyl, propane-1,2-diyl, propane-1,1-diyl, n-butane-1,4-diyl, n-butane-1,3-diyl, n-butane-1,2-diyl, n-butane-1,1-diyl, 2-methylpropane-1,3-diyl, 2-methylpropane-1,2-diyl, 2-methylpropane-1,1-diyl, 2-methylbutane-1,4-diyl, 2-methylbutane-2,4-diyl, 2-methylbutane-3,4-diyl, 2-methylbutane-4,4-diyl, 2-methylbutane-1,3-diyl, 2-methylbutane-1,2-diyl, 2-methylbutane-1,1-diyl or 2-methylbutane-2,3-diyl.

Among them, $R^1$ in the Chemical Formula 1, may be methane-1,1-diyl, propane-1,3-diyl, propane-1,2-diyl, propane-1,1-diyl, n-butane-1,4-diyl, n-butane-1,3-diyl, n-butane-1,2-diyl, n-butane-1,1-diyl, 2-methylpropane-1,3-diyl, 2-methylpropane-1,2-diyl, 2-methylpropane-1,1-diyl, 2-methylbutane-1,4-diyl, 2-methylbutane-2,4-diyl, 2-methylbutane-3,4-diyl, 2-methylbutane-4,4-diyl, 2-methylbutane-1,3-diyl, 2-methylbutane-1,2-diyl, 2-methylbutane-1,1-diyl or 2-methylbutane-2,3-diyl.

Specifically, $R^1$ in the Chemical Formula 1, may be methane-1,1-diyl, propane-1,3-diyl, or propane-1,2-diyl. More specifically, $R^1$ in the Chemical Formula 1, may be methane-1,1-diyl, or propane-1,2-diyl so as to improve the permeability calculated by the above Calculation Formula 1, and may be propane-1,3-diyl or propane-1,2-diyl so as to secure more excellent centrifuge retention capacity.

The compound of the Chemical Formula 1 wherein $R^1$ is one of the above listed divalent organic groups may provide an internal crosslink structure of which degradability by heat energy can be easily controlled, and it may not generate by-products or water-soluble components that change the properties of superabsorbent polymer after degradation.

The internal crosslinking agent may further comprise existing internal crosslinking agents known in the technical field to which the present invention pertains, in addition to the compound of the Chemical Formula 1. As the existing internal crosslinking agent, compounds comprising two or more crosslinkable functional groups in the molecule may be used. The existing internal crosslinking agent may comprise a carbon-carbon double bond as the crosslinkable functional group for the smooth crosslinking polymerization of the above explained water soluble ethylenically unsaturated monomers. Specifically, as the existing internal crosslinking agent, one or more selected from the group consisting of polyethyleneglycol diacrylate (PEGDA), glycerin diacrylate, glycerin triacrylate, non-modified or ethoxylated trimethylolpropane, triacrylate (TMPTA), hexanediol diacrylate, allyl (meth)acrylate and triethyleneglycol diacrylate may be used.

The internal crosslinking agent may comprise the compound of the Chemical Formula 1 in the content of 1 to 100 wt % or 50 to 100 wt %, based on the total weight of the internal crosslinking agent, and may comprise the remaining amount of the existing internal crosslinking agents, so as to have crosslinking density gradient of the aimed level. However, in order to provide superabsorbent polymer having simultaneously improved centrifuge retention capacity and absorbency under load, and exhibiting excellent heat stability, as the internal crosslinking agent, the compound represented by the Chemical Formula 1 may be used. That is, the internal crosslinking agent may comprise the compound of the Chemical Formula 1 in the content of 100 wt %.

And, the internal crosslinking agent may be used in the content of 0.01 to 5 parts by weight, 0.01 to 3 parts by weight, 0.1 to 3 parts by weight, or 0.2 to 1.5 parts by weight, based on 100 parts by weight of the water soluble ethylenically unsaturated monomers. Here, the content of the water soluble ethylenically unsaturated monomers is based on the weight of the water soluble ethylenically unsaturated monomers before the acidic groups of the monomers having acidic groups included in the water soluble ethylenically unsaturated monomers are neutralized. For example, in case the water soluble ethylenically unsaturated monomers include acrylic acid, the content of the internal crosslinking agent may be controlled on the basis of the weight of the monomer before acrylic acid is neutralized.

And, the internal crosslinking agent may be used in an appropriate concentration, based on the monomer mixture.

The internal crosslinking agent may be used within the above explained ranges to provide superabsorbent polymer that has a suitable crosslinking density gradient, and thus, has simultaneously improved centrifuge retention capacity and permeability.

The superabsorbent polymer according to one embodiment may be prepared in the presence of inorganic material, to exhibit excellent absorption properties.

As the inorganic material, for example, montmorillonite, saponite, nontronite, laponite, beidelite, hectorite, sauconite, stevensite, vermiculite, volkonskoite, magadite, medmontite, kenyaite, kaolin mineral, serpentine mineral, mica mineral, chlorite mineral, sepolite, palygorskite, bauxite silica, alumina, titania or a mixture thereof may be used.

Among them, laponite can effectively improve both centrifuge retention capacity and permeability.

The organic material may be added in the amount of about 0.001 to 1.0 wt %, based on the monomer mixture, to realize excellent absorption properties.

And, the monomer mixture may further comprise a polymerization initiator commonly used in the preparation of superabsorbent polymer.

Specifically, the polymerization initiator may be appropriately selected according to polymerization methods, a thermal polymerization initiator may be used when a thermal polymerization method is used, a photopolymerization initiator may be used when a photopolymerization method is used, and both thermal polymerization initiator and photopolymerization initiator may be used when a hybrid polymerization method (method using both heat and light) is used. However, even in the case of photopolymerization, since a certain amount of heat is generated by UV irradiation, etc., and heat is generated to some degree according to the progression of an exothermic polymerization reaction, a thermal polymerization initiator may be additionally included.

The photopolymerization initiator is not limited in terms of its construction, as long as it is a compound capable of forming a radical by light such as UV.

As the photopolymerization initiator, one or more selected from the group consisting of benzoin ether, dialkyl acetophenone, hydroxyl alkylketone, phenyl glyoxylate, benzyl dimethyl ketal, acyl phosphine, and α-aminoketone may be used. Specific example of the acyl phosphine may include diphenyl(2,4,6-trimethylbenzoyl)phosphine oxide, phenyl-bis(2,4,6-trimethylbenzoyl)phosphine oxide, ethyl (2,4,6-trimethylbenzoyl)phenylphosphinate, etc. More various photopolymerization initiators are described in Reinhold Schwalm, "UV Coatings: Basics, Recent Developments and New Application (Elsevier 2007)", page 115, and are not limited to the above described examples.

The photopolymerization initiator may be added in the concentration of about 0.0001 to about 2.0 wt %, based on the monomer composition. If the concentration of the photopolymerization initiator is too low, polymerization speed may become slow, and if the concentration of the polymerization initiator is too high, the molecular weight of the superabsorbent polymer may become small and the properties may become non-uniform.

And, as the thermal polymerization initiator, at least one selected from the group consisting of a persulfate initiator, an azo initiator, hydrogen peroxide, and ascorbic acid may be used. Specific examples of the persulfate initiator may include sodium persulfate ($Na_2S_2O_8$), potassium persulfate ($K_2S_2O_8$), ammonium persulfate (($NH_4)_2S_2O_8$), etc., and, specific examples of the azo initiator may include 2,2-azobis (2-amidinopropane)dihydrochloride, 2,2-azobis-(N,N-dimethylene)isobutyramidinedihydrochloride, 2-(carbamoylazo)isobutyronitril, 2,2-azobis[2-(2-imidazolin-2-yl) propane]dihydrochloride, 4,4-azobis-(4-cyanovalericacid), etc. More various thermal initiators are described in "Principle of Polymerization (Wiley, 1981)", Odian, page 203, and are not limited to the above described examples.

The thermal polymerization initiator may be included in the concentration of about 0.001 to about 2.0 wt %, based on the monomer composition. If the concentration of the thermal polymerization initiator is too low, additional thermal polymerization may hardly occur, and thus, the effect obtained by the addition of the thermal polymerization initiator may be insignificant, and if the concentration of the thermal polymerization initiator is too high, the molecular weight of the superabsorbent polymer may become small, and the properties may become non-uniform.

The monomer mixture may further comprise additives such as a thickener, a plasticizer, a preservation stabilizer, an antioxidant, etc., as necessary.

The above explained raw materials such as water soluble ethylenically unsaturated monomers, an internal crosslinking agent, inorganic material, a polymerization initiator and additives may be prepared in the form of a solution dissolved in a solvent.

Here, the solvent that can be used is not limited in terms of its construction as long as it can dissolve or disperse the above explained components, and for example, one or more selected from water, ethanol, ethyleneglycol, diethyleneglycol, triethyleneglycol, 1,4-butanediol, propyleneglycol, ethyleneglycol monobutyl ether, propyleneglycol monomethyl ether, propyleneglycol monomethyl ether acetate, methylethylketone, acetone, methylamylketone, cyclohexanone, cyclopentanone, diethyleneglycol monomethyl ether, diethyleneglycol ethyl ether, toluene, xylene, butyrolactone, carbitol, methylcellosolve acetate and N,N-dimethylacetamide, etc. may be used alone or in combination.

The solvent may be included in the remaining amount excluding the above-explained components, based on the total amount of the monomer mixture.

Meanwhile, a method of forming hydrogel polymer by the thermal polymerization, photopolymerization or hybrid polymerization of the monomer composition is not specifically limited in terms of its construction, as long as it is a commonly used polymerization method.

Specifically, the polymerization method is largely classified into thermal polymerization and photopolymerization according to energy source. Commonly, thermal polymerization may be progressed in a reactor equipped with a stirring axis such as a kneader, and, in case thermal polymerization is progressed, it may be progressed at a temperature of about 80° C. or more and less than about 110° C. so that the compound represented by the Chemical Formula 1 may not be degraded by heat. A means to achieve the polymerization temperature of the above explained range is not specifically limited, and a heating medium may be supplied to the reactor or a heat source may be directly supplied to heat. The kinds of the heating medium that can be used may include temperature-raised fluid such as steam, hot air, hot oil, etc., but are not limited thereto, and may be appropriately selected considering the means of the heating medium, temperature rise speed and target temperature to be increased. Meanwhile, the heat source directly supplied may include electric heating, gas heating, etc., but is not limited thereto.

Meanwhile, photopolymerization may be progressed in a reactor equipped with a movable conveyer belt, but the above explained polymerization methods are no more than examples, and the present invention is not limited thereto.

For example, in case thermal polymerization is progressed by supplying a heating medium into a reactor equipped with a stirring axis such as a kneader as explained above or heating the reactor, hydrogel polymer discharged to the outlet of the reactor may be obtained. The hydrogel polymer may be obtained in the size of a few centimeters to a few millimeters according to the shape of the stirring axis equipped in the reactor. Specifically, the size of obtained hydrogel polymer may vary according to the concentration of the introduced monomer mixture and the introduction speed, etc.

And, in case photopolymerization is progressed in a reactor equipped with a movable conveyer belt as explained above, the obtained hydrogel polymer may be in the form of a sheet having the width of the belt. Here, the thickness of the polymer sheet may vary according to the concentration of the introduced monomer mixture and the introduction speed, but, commonly, a monomer mixture is preferably fed such that polymer in the form of a sheet having a thickness of about 0.5 cm to about 10 cm may be obtained. In case a monomer mixture is fed such that the thickness of sheet-shaped polymer may be too thin, production efficiency may be low, and if the thickness of the sheet-shaped polymer is greater than 10 cm, due to the too thick thickness, a polymerization reaction may not uniformly occur throughout the whole thickness.

The polymerization time of the monomer mixture is not specifically limited, and it may be controlled to about 30 seconds to 60 minutes.

Here, the moisture content of hydrogel polymer obtained by such a method may be about 30 to about 80 wt %. Throughout the specification, the "moisture content" is the content of moisture occupied based on the total weight of hydrogel polymer, and it means a value obtained by subtracting the weight of polymer of a dry state from the weight of hydrogel polymer. Specifically, it is defined as a value calculated by measuring the weight loss according to moisture evaporation in the polymer while raising the temperature of polymer through infrared heating to dry. At this time, the drying condition is set up such that the temperature is raised from room temperature to about 180° C. and then maintained at 180° C., and the total drying time is 20 minutes including a temperature raising step of 5 minutes.

In the step of forming base resin powder, the hydrogel polymer obtained through the step of forming hydrogel polymer is dried to provide base resin powder.

In the step of forming base resin powder, a coarse grinding process may be included before drying the hydrogel polymer so as to increase drying efficiency.

Here, grinders that can be used in the coarse grinding is not limited in terms of the constructions, but specifically, one selected from the group consisting of a vertical pulverizer, a turbo cutter, a turbo grinder, a rotary cutter mill, a cutter mill, a disc mill, a shred crusher, a crusher, a chopper, a disc cutter may be used, but is not limited thereto.

Through the coarse grinding step, the particle diameter of the hydrogel polymer may be controlled to about 0.1 to about 10 mm. Grinding to a particle diameter of less than 0.1 mm would not be technically easy due to the high moisture content of the hydrogel polymer, and may generate agglomeration between the ground particles. Meanwhile, if grinding to a particle diameter greater than 10 mm, the effect of increasing the efficiency of the subsequent drying step may be insignificant.

The hydrogel polymer coarsely ground as explained above, or hydrogel polymer immediately after polymerization that does not pass through the coarse grinding step is dried, and the drying temperature may be about 20° C. to about 250° C. If the drying temperature is less than about 20° C., a drying time may too lengthen, and the properties of the finally prepared superabsorbent polymer may be deteriorated, and if the drying temperature is greater than about 250° C., only the surface of hydrogel polymer may be dried, thus generating fine powder in the subsequent grinding process, and the properties of the finally prepared superabsorbent polymer may be deteriorated. Preferably, the drying may be progressed at a temperature of about 40 to 200° C., more preferably at 110 to 200° C.

Particularly, if the drying temperature of the hydrogel polymer is about 110° C. to about 200° C., at least a part of the crosslink structure derived from the compound represented by the Chemical Formula 1 may be degraded by heat. As the result, the internal crosslinking density of the crosslinked polymer may decrease in the drying step. Such crosslinked polymer with decreased internal crosslinking density may provide superabsorbent polymer with remarkably improved centrifuge retention capacity, compared to the crosslinked polymer of which internal crosslinking density has not decreased.

Meanwhile, the drying may be progressed for 20 minutes to 120 minutes considering the process efficiency, etc. For example, the hydrogel polymer may be dried for about 20 minutes to 100 minutes or about 30 minutes to about 50 minutes, so that the internal crosslink structure may be sufficiently degraded.

And, the drying method is not limited in terms of the construction as long as it can be commonly used as a drying process of hydrogel polymer. Specifically, the drying step may be progressed by hot wind supply, infrared ray irradiation, ultrahigh frequency wave irradiation, or UV irradiation, etc. The polymer dried by such a method may exhibit a moisture content of about 0.1 to about 10 wt %.

The step of forming base resin powder may further comprise a step of grinding the dried polymer obtained through the drying step.

The particle diameter of the polymer powder obtained after the grinding step may be 150 μm to 850 μm. As a grinder for grinding to such a particle diameter, specifically, a pin mill, a hammer mill, a screw mill, a roll mill, a disc mill, or a jog mill, etc. may be used, but the grinder is not limited thereto.

And, the step of forming base resin powder may further comprise a step of sieving the ground polymer obtained through the grinding step. That is, in the step of forming base resin powder, the hydrogel polymer may be dried, ground and sieved to provide base resin powder.

After the grinding step, a step of sieving the polymer powder according to the particle diameter may be conducted so as to manage the properties of the finally productized superabsorbent polymer. It is appropriate that base resin powder and superabsorbent polymer obtained therefrom are prepared and provide with particle diameters of about 150 to 850 μm, through the processes of grinding and sieving, etc. More specifically, at least about 95% of the base resin powder and superabsorbent polymer obtained therefrom may have particle diameters of about 150 to 850 μm, and less than about 3 wt % thereof may be fine powder with particle diameters of less than about 150 μm As explained, since the particle diameter distributions of the base resin powder and superabsorbent polymer are controlled within preferable ranges, the finally prepared superabsorbent polymer may exhibit excellent absorption properties. Thus, in the sieving step, polymer with particle diameters of about 150 to about 850 μm may be sieved, and only the polymer powders having such particle diameters may be subjected to surface crosslinking and productized.

Meanwhile, after forming the base resin powder, in the presence of a surface crosslinking agent, the surface of the base resin powder may be additionally crosslinked to form a surface crosslink layer, thereby preparing superabsorbent polymer.

As the surface crosslinking agent, any surface crosslinking agents used for the preparation of superabsorbent polymer before may be used without specific limitations. Specific examples thereof may include one or more polyols selected from the group consisting of ethyleneglycol, propylene glycol, 1,3-propanediol, 1,4-butanediol, 1,6-hexanediol, 1,2-hexanediol, 1,3-hexanediol, 2-methyl-1,3-propanediol, 2,5-hexanediol, 2-methyl-1,3-pentandiol, 2-methyl-2,4-pentanediol, tripropylene glycol and glycerol; one or more carbonate-based compounds selected from the group consisting of ethylene carbonate and propylene carbonate; epoxy compounds such as ethyleneglycol diglycidylether, etc.; oxazoline compounds such as oxazolidinone, etc.; polyamine compounds; oxazoline compounds; mono-, di-, or polyoxazolidinone compounds; or cyclic urea compounds, etc.

Such a surface crosslinking agent may be used in the content of about 0.01 to 3 parts by weight, 0.10 to 1 parts by weight, or 0.10 to 0.30 parts by weight, based on 100 parts by weight of the base resin powder. By controlling the content range of the surface crosslinking agent within the above explained range, superabsorbent polymer exhibiting excellent absorption properties may be provided.

And, in the surface crosslinking process, in addition to the surface crosslinking agent, one or more inorganic materials selected from the group consisting of silica, clay, alumina, silica-alumina composite, titania, zinc oxide and aluminum sulfate may be further added to conduct a surface crosslinking reaction. The inorganic material may be used in the form of powder or liquid, and particularly, in the form of alumina powder, silica-alumina powder, titania powder, or nano silica solution. And, the inorganic material may be used in the content of about 0.001 to about 2 parts by weight, based on 100 parts by weight of the base resin powder.

And, in the surface crosslinking process, instead of or in addition to the inorganic material, multivalent metal cation may be added to progress surface crosslinking, thereby optimizing the surface crosslink structure of superabsorbent polymer. It is predicted that such metal cation may form chelate with the carboxy group (COOH) of superabsorbent polymer, thus further reducing the crosslinking distance.

And, the method of adding the surface crosslinking agent to base resin powder is not limited in terms of its construction. For example, a surface crosslinking agent and base resin powder may be put in a reactor and mixed, a surface crosslinking agent may be sprayed to base resin powder, or base resin powder and a surface crosslinking agent may be continuously fed to a continuously operated mixed and mixed.

When the surface crosslinking agent is added, water and methanol may be mixed together and added. In case water and methanol are added, the surface crosslinking agent may be uniformly dispersed in the base resin powder. Here, the content of water added may be controlled to about 1 to 20 parts by weight, 5 to 15 parts by weight, or 5 to 10 parts by weight, based on 100 parts by weight of the base resin powder, and the content of methanol added may be controlled to about 1 to 20 parts by weight, 5 to 15 parts by weight, or 5 to 10 parts by weight, based on 100 parts by weight of the base resin powder. Within such ranges, uniform dispersion of the surface crosslinking agent may be induced, the agglomeration of the base resin powder may be prevented, and the surface penetration depth of the crosslinking agent may be optimized.

For example, in the surface crosslinking process, a surface crosslinking solution comprising, based on 100 parts by weight of the base resin powder, 0.10 to 1 parts by weight or 0.10 to 0.30 parts by weight of a surface crosslinking agent, 5 to 15 parts by weight of water, and 5 to 15 parts by weight of methanol, may be used to provide superabsorbent polymer having excellent permeability calculated by the above Calculation Formula 1.

Meanwhile, by heating the base resin powder to which the surface crosslinking agent is added beyond a specific temperature, a surface crosslinking reaction may be achieved. In such a surface crosslinking step, an internal crosslink degradation reaction may be achieved simultaneously with the surface crosslinking reaction. Thus, in the surface crosslinking step, at least a part of the crosslink structure derived from the compound of the Chemical Formula 1 in the base resin powder may be heat degraded, and thus, internal crosslinking density may decrease. And, due to the above reactions, superabsorbent polymer with a crosslinking density gradient increasing from the inside toward the outside may be prepared.

Particularly, in order to prepare superabsorbent polymer with simultaneously improved centrifuge retention capacity and permeability, the surface crosslinking reaction may be conducted at a temperature of about 110 to 200° C.

More specifically, the surface crosslinking conditions may include a maximum reaction temperature of about 160° C. or more, or about 180 to 200° C., and a maintenance time at the maximum reaction temperature of about 20 minutes or more, or about 20 minutes to 2 hours. And, a time during which a temperature is increased from the temperature at the beginning of the reaction, for example, about 110° C. or more, or about 160 to 170° C., to the above maximum reaction temperature, may be controlled to about 10 minutes or more, or about 10 minutes to 1 hour, and it was confirmed that superabsorbent polymer with simultaneously excellent centrifuge retention capacity and permeability may be prepared by satisfying the above explained surface crosslinking process conditions.

A temperature rise means for the surface crosslinking reaction is not specifically limited. A heating medium may be supplied, or a heat source may be directly supplied to heat. Here, the kinds of the heating medium that can be used may include temperature-increased fluid such as steam, hot air, hot oil, etc., but are not limited thereto, and may be appropriately selected considering the means of the heating medium, temperature rise speed and a temperature to be increased. Meanwhile, the heat source directly supplied may include electric heating, gas heating, etc., but is not limited thereto.

The superabsorbent polymer obtained according to the above explained preparation method has a crosslinking density increasing from the inside toward the outside because a part of the heat-degradable internal crosslink structure is degraded in the subsequent process of high temperature after the polymerization process, and thus, it may exhibit very excellent properties with simultaneously improved centrifuge retention capacity and permeability, etc.

Since the superabsorbent polymer according to one embodiment of the present invention simultaneously exhibits excellent centrifuge retention capacity and permeability, it can fundamentally solve the problems of the existing superabsorbent polymer technical requirement of the art, and can provide various hygienic goods exhibiting more excellent properties.

DETAILED DESCRIPTION OF THE EMBODIMENTS

Hereinafter, the actions and the effects of the invention will be explained in detail through the specific examples. However, these examples are presented only as the illustrations of the invention, and the scope of the right of the invention is not limited thereby.

Example 1: Preparation of Superabsorbent Polymer

Into a glass reactor, 100 g of acrylic acid, 0.6 g of 4-methylpentane-1,4-diyl diacrylate, 0.008 g of Irgacure TPO (diphenyl(2,4,6-trimethylbenzoyl)phosphine oxide), 0.18 g of laponite and 55 g of water were put. And, to the glass reactor, 123.5 g of 32 wt % caustic soda solution was slowly added dropwise and mixed.

When adding the caustic soda solution dropwise, the temperature of the mixed solution increased by neutralization heat, thus waited until the mixed solution was cooled. When the temperature of the mixed solution was cooled to about 45° C., 0.2 g of sodium persulfate was added to the mixed solution to prepare a monomer mixture.

On a conveyer belt with a width of 10 cm and a length of 2 m, rotating at the velocity of 50 cm/min, the monomer mixture was fed at 500~2000 mL/min. And, simultaneously with the feeding of the monomer mixture, UV was irradiated at the intensity of 10 mW/cm$^2$ to progress a polymerization reaction for 60 seconds.

And, the polymer obtained through the polymerization reaction was passed through a hole with a diameter of 10 mm to prepare as crumb using a meat chopper. Subsequently, the crumb was uniformly dried by flowing hot air of 185° C. from the lower part to the upper part for 20 minutes using an oven capable of transferring air volume upward and downward, and flowing it again from the upper part to the lower part for 20 minutes. The dried crumb was ground with a grinder, and then, sieved to obtain base resin with a size of 150 to 850 μm.

To 100 g of the above prepared base resin powder, a mixed solution of 8 g of deionized water, 8 g of methanol, 0.2 g of ethylene carbonate, and 0.01 g of silica (product name: REOLOSIL DM30S, manufacturing company: Tokuyama Corporation) was added, and mixed for 1 minute, and then, surface crosslinking was conducted at 185° C. for 90 minutes.

And, the obtained product was ground and sieved to obtain superabsorbent polymer with a particle diameter of 150 to 850 μm.

Example 2: Preparation of Superabsorbent Polymer

Superabsorbent polymer was prepared by the same method as Example 1, except that 0.6 g of 2-methylpentane-2,4-diyl diacrylate was used instead of 0.6 g of 4-methylpentane-1,4-diyl diacrylate in Example 1.

Example 3: Preparation of Superabsorbent Polymer

Superabsorbent polymer was prepared by the same method as Example 1, except that 0.6 g of 2-methylpropane-1,2-diyl diacrylate was used instead of 0.6 g of 4-methylpentane-1,4-diyl diacrylate in Example 1.

Example 4: Preparation of Superabsorbent Polymer

Superabsorbent polymer was prepared by the same method as Example 1, except that 0.6 g of 2-methylbutane-2,4-diyl diacrylate was used instead of 0.6 g of 4-methylpentane-1,4-diyl diacrylate in Example 1.

Comparative Example 1: Preparation of Superabsorbent Polymer

Superabsorbent polymer was prepared by the same method as Example 1, except that laponite was not introduced.

Comparative Example 2: Preparation of Superabsorbent Polymer

Superabsorbent polymer was prepared by the same method as Example 4, except that laponite was not introduced.

Experimental Example: Evaluation of the Properties of Superabsorbent Polymer

The properties of the superabsorbent polymers prepared according to Examples and Comparative Examples were evaluated as follows, and shown in the following Table 1.
(1) Permeability (Perm)
For the superabsorbent polymers prepared according to Examples and Comparative Examples, permeabilities were measured according to the following Calculation Formula 1.

$$\text{Perm} = [20 \text{ mL}/T_1 \text{ (sec)}] * 60 \text{ sec} \quad \text{[Calculation Formula 1]}$$

in the Calculation Formula 1,

Perm is the permeability of superabsorbent polymer, and $T_1$ is a time (seconds) taken for a saline solution of 20 mL to pass through swollen superabsorbent polymer under pressure of 0.3 psi, after putting 0.2 g of superabsorbent polymer in a cylinder, and pouring a saline solution (0.9 wt % sodium chloride aqueous solution) so that the superabsorbent polymer is completely submerged, thus swelling the superabsorbent polymer for 30 minutes.

Specifically, a cylinder and a piston were prepared. As the cylinder, a cylinder having an inner diameter of 20 mm, and equipped with a glass filter and a stopcock at the bottom was used. As the piston, a piston wherein a screen that has an outer diameter slightly smaller than 20 mm, and thus, can freely move the cylinder upward and downward, is positioned at the bottom, a weight is positioned at the top, and the screen and weight are connected by a rod, was used. In the piston, a weight capable of adding a pressure of 0.3 psi due to the addition of the piston was installed.

While the stopcock of the cylinder was locked, 0.2 g of superabsorbent polymer was put, and an excessive amount of a saline solution (0.9 wt % of a sodium chloride aqueous solution) was poured such that the superabsorbent polymer was completely submerged. And, the superabsorbent polymer was swollen for 30 minutes. Thereafter, on the swollen superabsorbent polymer, a piston was added to uniformly give a load of 0.3 psi.

Subsequently, the stopcock of the cylinder was opened and a time for 20 mL of the saline solution to pass through the swollen superabsorbent polymer was measured (unit: second). Here, if the meniscus is marked when 40 mL of the saline solution is filled in the cylinder and the meniscus is marked when 20 mL of the saline solution is filled in the cylinder, the $T_1$ of the Calculation Formula 1 can be easily measured by measuring a time taken to reach the level corresponding to 20 ml from the level corresponding to 40 mL.

(2) Centrifuge Retention Capacity (CRC)

The centrifuge retention capacity (CRC) of the superabsorbent polymer to a saline solution was measured according to EDANA method NWSP 241.0.R2.

Specifically, among the superabsorbent polymer of which centrifuge retention capacity is to be measured, a sample with the particle diameter of 150 to 850 μm, which passes through a US standard 20 mesh screen, and remains on a US standard 100 mesh screen, was prepared.

And, $W_0$ (g, about 0.2 g) of the sample having a particle diameter of 150 to 850 μm were uniformly put in an envelope made of non-woven fabric, and the envelope was sealed. And, the envelope was soaked in a 0.9 wt % sodium chloride aqueous solution (saline solution) at room temperature. After 30 minutes, the envelope was drained at 250 G for 3 minutes using a centrifuge, and then, the mass $W_2$ (g) of the envelope was measured. And, after the same operation using an empty envelope without a sample, the mass $W_1$ (g) at that time was measured.

Using the obtained weights, CRC (g/g) was calculated according to the following Calculation Formula 2.

CRC (g/g)={[$W_2$(g)−$W_1$(g)]/$W_0$(g)}−1   [Calculation Formula 2]

In the Calculation Formula, $W_0$ (g) is the initial weight of the sample having a particle diameter of 150 to 850 μm(g), $W_1$ (g) the weight of an empty envelope made of non-woven fabric, measured after the empty envelope without a sample was soaked in a saline solution at room temperature for 30 minutes, and then, drained using a centrifuge at 250 G for 3 minutes, and $W_2$ (g) is the weight of an envelope made of nonwoven fabric including the sample, measured after the envelope made of nonwoven fabric including the sample was soaked in a saline solution at room temperature for 30 minutes, and then, drained using a centrifuge at 250 G for 3 minutes.

(3) Absorbency Under Load (AUL)

The absorbency under load (AUL) of 0.7 psi of the superabsorbent polymer to a saline solution was measured according to EDANA method NWSP 242.0.R2.

Specifically, a 400 mesh screen made of stainless was installed on the bottom of a plastic cylinder with an inner diameter of 25 mm. Under the conditions of room temperature and relative humidity of 50%, $W_0$ (g, 0.16 g) of superabsorbent polymer of which absorbency under load is to be measured were uniformly scattered on the screen. Subsequently, a piston that can uniformly give a load of 4.8 kPa (0.7 psi) was added on the superabsorbent polymer. Here, as the piston, a piston having an outer diameter slightly smaller than 25 mm was used such that there was no gap with the inner wall of the cylinder, and the movement upward and downward was not hindered. At this time, the weight $W_3$ (g) of the apparatus was measured.

Subsequently, on the inner side of a petri dish with a diameter of 150 mm, a glass filter with a diameter of 90 mm and a thickness of 5 mm was positioned, and a 0.90 wt % sodium chloride aqueous solution (saline solution) was poured on the petri dish. Here, the saline solution was poured until the water level of the saline solution became horizontal to the upper side of the glass filter. And, one filter paper with a diameter of 90 mm was put thereon.

Subsequently, the above prepared apparatus was mounted on the filter paper so that the superabsorbent polymer in the apparatus was swollen by the saline solution under load. After 1 hour, the weight $W_4$ (g) of the apparatus including swollen superabsorbent polymer was measured.

Using the measured weights, absorbency under load was calculated according to the following Calculation Formula 3.

AUL (g/g)=[$W_4$(g)−$W_3$(g)]/$W_0$(g)   [Calculation Formula 3]

In the Formula 3, $W_0$ (g) is the initial weight (g) of superabsorbent polymer, $W_3$ (g) is the sum of the weight of superabsorbent polymer and the weight of the apparatus capable of giving load to the superabsorbent polymer, and $W_4$ (g) is the sum of the weight of superabsorbent polymer and the weight of the apparatus capable of giving load to the superabsorbent polymer, after a saline solution is absorbed in the superabsorbent polymer under load (0.7 psi) for 1 hour.

TABLE 1

|  | Perm [mL] | CRC [g/g] | AUL (0.7 psi) [g/g] |
| --- | --- | --- | --- |
| Example 1 | 17 | 34.0 | 25.7 |
| Example 2 | 24 | 32.5 | 25.8 |
| Example 3 | 25 | 32.2 | 25.3 |
| Example 4 | 16 | 31.7 | 24.5 |
| Comparative Example 1 | 15 | 33.1 | 25.2 |
| Comparative Example 2 | 13 | 31.4 | 24.2 |

Referring to Table 1, it is confirmed that the superabsorbent polymers of Examples 1 to 4 wherein superabsorbent polymer was prepared in the presence of a heat-degradable internal crosslinking agent and inorganic material, have permeability calculated by the above Calculation Formula 1 of 16 mL/1 minute or more, and have both excellent centrifuge retention capacity and absorbency under load.

To the contrary, the superabsorbent polymers of Comparative Examples 1 and 2 wherein inorganic material was not used together with a heat-degradable internal crosslinking agent, exhibited low permeability calculated by the above Calculation Formula 1.

Meanwhile, comparing Example 1 and Comparative Example 1 using the same heat-degradable internal crosslinking agent, it is confirmed that Example 1 has excellent centrifuge retention capacity and absorbency under load, as well as excellent permeability, compared to Comparative Example 1. Similarly, comparing Example 4 and Comparative Example 2 using the same heat-degradable internal crosslinking agent, it is also confirmed that Example 4 have excellent centrifuge retention capacity and absorbency under load, as well as excellent permeability, compared to Comparative Example 2.

Meanwhile, comparing Examples 1 to 4, it is confirmed that among the compounds represented by the Chemical Formula 1, the compound wherein $R^1$ is methane-1,1-diyl (Example 3); propane-1,3-diyl(Example 1); or propane-1,2- diyl(Example 2) can realize high permeability while exhibiting relatively high centrifuge retention capacity.

What is claimed is:

1. A superabsorbent polymer comprising
a base resin powder comprising crosslinked polymer formed by the crosslinking polymerization, in an aqueous solution, of water soluble ethylenically unsaturated monomers having acid groups of which at least a part are neutralized, in the presence of an internal crosslinking agent comprising a compound represented by the following Chemical Formula 1, and inorganic material; and
a surface crosslink layer on the base resin powder, formed by the additional crosslinking of the crosslinked polymer,
wherein the inorganic material is montmorillonite, saponite, nontronite, laponite, beidelite, hectorite, sauconite, stevensite, vermiculite, volkonskoite, magadite, medmontite, kenyaite, kaolin mineral, serpentine mineral, mica mineral, chlorite mineral, sepolite, palygorskite, bauxite silica, alumina, titania or a mixture thereof,
wherein the permeability calculated by the following Calculation Formula 1 is equal to or greater than 17 mL/1 minute:

[Chemical Formula 1]

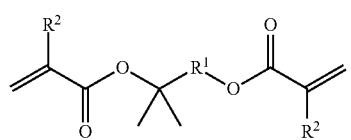

in the Chemical Formula 1, $R^1$ is a divalent organic group derived from C1-10 alkane, and $R^2$ is hydrogen or a methyl group, wherein $R^1$ in the Chemical Formula 1, is methane-1,1-diyl, propane-1,3-diyl, propane-1,2-diyl, propane-1,1-diyl, n-butane-1,4-diyl, n-butane-1,3-diyl, n-butane-1,2-diyl, n-butane-1,1-diyl, 2-methylpropane-1,3-diyl, 2-methylpropane-1,2-diyl, 2-methylpropane-1,1-diyl, 2-methylbutane-1,4-diyl, 2-methylbutane-2,4-diyl, 2-methylbutane-3,4-diyl, 2-metylbutane-4,4-diyl, 2-methylbutane-1,3-diyl, 2-methylbutane-1,2-diyl, 2-methylbutane-1,1-diyl or 2-methylbutane-2,3-diyl, Perm=[20 mL/$T_1$ (sec)]*60 sec [Calculation Formula 1]

in the Calculation Formula 1,
Perm is the permeability of superabsorbent polymer, and $T_1$ is a time (seconds) taken for a saline solution of 20 mL to pass through swollen superabsorbent polymer under pressure of 0.3 psi, after putting 0.2 g of superabsorbent polymer in a cylinder, and pouring a saline solution (0.9 wt % sodium chloride aqueous solution) so that the superabsorbent polymer is completely submerged, thus swelling the superabsorbent polymer for 30 minutes.

2. The superabsorbent polymer according to claim 1, wherein centrifuge retention capacity(CRC) to a saline solution is 32 to 40 g/g, and absorbency under load(AUL) of 0.7 psi to a saline solution is 25 to 30 g/g.

3. The superabsorbent polymer according to claim 1, wherein $R^1$ in the Chemical Formula 1, is methane-1,1-diyl, propane-1,3-diyl or propane-1,2-diyl.

4. The superabsorbent polymer according to claim 1, wherein the surface crosslink layer is formed using a surface crosslinking solution comprising, based on 100 parts by weight of the base rein powder, 0.10 to 1 parts by weight of a surface crosslinking agent, 5 to 15 parts by weight of water, and 5 to 15 parts by weight of methanol.

* * * * *